(12) United States Patent
Deem et al.

(10) Patent No.: US 7,314,484 B2
(45) Date of Patent: Jan. 1, 2008

(54) METHODS AND DEVICES FOR TREATING ANEURYSMS

(75) Inventors: Mark Deem, Mountain View, CA (US); Hanson S. Gifford, III, Woodside, CA (US); Bernard Andreas, Redwood City, CA (US); Sunmi Chew, San Jose, CA (US); Ron French, Santa Clara, CA (US); Doug Sutton, Pacifica, CA (US)

(73) Assignee: The Foundry, Inc., Menlo Park, CA (US)

( * ) Notice: Subject to any disclaimer, the term of this patent is extended or adjusted under 35 U.S.C. 154(b) by 0 days.

(21) Appl. No.: 10/612,833

(22) Filed: Jul. 1, 2003

(65) Prior Publication Data

US 2004/0073190 A1 Apr. 15, 2004

Related U.S. Application Data

(60) Provisional application No. 60/393,697, filed on Jul. 2, 2002.

(51) Int. Cl.
*A61F 2/06* (2006.01)

(52) U.S. Cl. ..................... 623/1.36; 623/1.42

(58) Field of Classification Search ....... 623/1.35–1.48
See application file for complete search history.

(56) References Cited

U.S. PATENT DOCUMENTS

| 5,197,977 A * | 3/1993 | Hoffman et al. ........... 623/1.45 |
| 5,795,331 A | 8/1998 | Cragg et al. |
| 5,824,054 A | 10/1998 | Khosravi et al. |
| 6,093,199 A | 7/2000 | Brown et al. |
| 7,147,656 B2 * | 12/2006 | Andreas et al. ........... 623/1.11 |
| 2002/0013620 A1 * | 1/2002 | Kujawski ................... 623/1.16 |
| 2002/0058993 A1 | 5/2002 | Landau et al. |
| 2002/0065546 A1 | 5/2002 | Machan et al. |

(Continued)

FOREIGN PATENT DOCUMENTS

WO WO 00/56283 9/2000

(Continued)

OTHER PUBLICATIONS

Curci et al., "Pharmacologic suppression of experimental abdominal aortic aneurysms: A comparison of doxycycline and four chemically modified tetracyclines," Journal of Vascular Surgery, 1998, vol. 28, No. 6, 1082-1093.

(Continued)

*Primary Examiner*—Suzette Gherbi
(74) *Attorney, Agent, or Firm*—Townsend and Townsend and Crew LLP (57) ABSTRACT

Methods and devices provide delivery of one or more therapeutic agents to a treatment site at or near an aneurysm, such as an abdominal aortic aneurysm ("AAA"). Methods typically include placing a device at or near the AAA and releasing one or more therapeutic agents from the device. This may also involve releasing multiple agents in sequential fashion. Examples of possible therapeutic agents include doxycycline, roxithromycin, tetracycline, tetracycline derivatives, and collagen promoting agents, such as propranolol. Devices used to deliver one or more therapeutic agents may include stents, grafts, stent grafts, balloons with perforations and/or needles, expandable wire baskets, drug-eluting capsules, or suitable combinations thereof. One embodiment includes a stent graft with a distally-extending skirt and an supra-renal anchor.

16 Claims, 8 Drawing Sheets

U.S. PATENT DOCUMENTS

| | | | |
|---|---|---|---|
| 2003/0120338 A1* | 6/2003 | Chobotov et al. | 623/1.36 |
| 2003/0130720 A1* | 7/2003 | DePalma et al. | 623/1.13 |
| 2004/0082989 A1* | 4/2004 | Cook et al. | 623/1.13 |
| 2004/0117003 A1* | 6/2004 | Ouriel et al. | 623/1.35 |
| 2004/0199241 A1* | 10/2004 | Gravett et al. | 623/1.13 |
| 2004/0210300 A1* | 10/2004 | Aboul-Hosn | 623/1.23 |
| 2004/0220653 A1* | 11/2004 | Borg et al. | 623/1.11 |
| 2005/0171599 A1* | 8/2005 | White | 623/1.36 |
| 2007/0142896 A1* | 6/2007 | Anderson et al. | 623/1.13 |

FOREIGN PATENT DOCUMENTS

| | | |
|---|---|---|
| WO | WO 02/13871 | 2/2002 |
| WO | WO 03/043539 | 5/2003 |

OTHER PUBLICATIONS

Lindholt et al., "Five-year Results of Elastin and Collagen Markers as Predictive Tools in the Management of Small Abdominal Aortic Aneurysms," Eur J Vasc Endovasc Surg, 2001, vol. 21, 235-240.

Lindholt et al., "Indicators of infection with *Chlamydia pneumoniae* are associated with expansion of abdominal aortic aneurysms," Journal of Vascular Surgery, 2001, vol. 34, No. 2, 212-215.

Neumann et al., "Treatment of *Chlamydia pneumoniae* infection with roxithromycin and effect on neointima proliferation after coronary stent placement (ISAR-3): a randomized, double-blind, placebo-controlled trial," The Lancet, 2001, vol. 357, 2085-2089.

Vammen et al., "Antibodies Against *Chlamydia pneumoniae* Predict the Need for Elective Surgical Intervention on Small Abdominal Aortic Aneurysms," Eur J Vasc Endovasc Surg, 2001, vol. 22, 165-168.

Vammen et al., "Randomized double-blind controlled trial of roxithromycin for prevention of abdominal aortic aneurysm expansion," British Journal of Surgery 2001, 88, 1066-1072.

White, "Are There Ways to Retard the Growth of Abdominal Aortic Aneurysms?" 2001 Clinical Congress p. 10, Session IIA: New Approaches to Old Problems: Vascular Disease, 2001, 30-33.

* cited by examiner

FIG_4B

METHODS AND DEVICES FOR TREATING ANEURYSMS

CROSS-REFERENCES TO RELATED APPLICATIONS

The present application is a non-provisional of U.S. patent application Ser. No. 60/393,697, filed Jul. 2, 2002, the full disclosure of which is incorporated herein by reference.

BACKGROUND OF THE INVENTION

The present invention relates to methods and devices for treating aneurysms. More particularly, the invention relates to methods and devices for treating abdominal aortic aneurysms by delivering one or more therapeutic agents at or near the aneurysm.

An aneurysm is a sac formed by localized dilatation of the wall of an artery, a vein, or the heart. Common areas where aneurysms occur and cause potential medical conditions include the coronary arteries, the carotid arteries, various cerebral arteries, and the abdominal aorta. When a local dilatation of a vessel occurs, irregular blood flow patterns result, typically leading to clot formation. Typically, the wall of the vessel also progressively dilates and weakens, often resulting in vessel rupture. Vessel rupture, in turn, often causes dramatic negative health consequences such as a stroke, when a cerebral vessel ruptures, or even death, when an abdominal aortic aneurysm ("AAA") ruptures. In light of these consequences, improved treatment methods and devices for aneurysms are constantly being sought. Although the following discussion focuses on AAA treatment, it is equally applicable to aneurysms in other locations.

Researchers have hypothesized that the development, expansion and rupture of AAAs are all related to connective tissue destruction. For a discussion of this hypothesis, see for example, "Pharmacologic suppression of experimental abdominal aortic aneurysms: A comparison of doxycycline and four chemically modified tetracyclines," Curci, John A., Petrinec, Drazen, et al., Journal of Vascular Surgery, December 1998, vol. 28, no. 6, 1082-1093 (hereinafter "Curci article"), the contents of which are hereby incorporated by reference. Connective tissue destruction, in turn, has been linked to the presence of a number of enzymes which break down blood vessel wall connective tissues such as elastin. Examples of such "elastolytic" enzymes include serine proteinases such as metalloproteinases ("MMPs"). It has been found that increased levels of MMPs and other elastolytic enzymes are typically present in AAAs.

Researchers have also found that AAAs and other aneurysmal vessels often contain elevated levels of the *Chlamydia pneumoniae* bacterium, which may be another cause of aneurysmal disease. Thus, AAA treatments focussing on drug therapy to combat MMPs and similar enzymes, to combat *C pneumoniae*, to generally suppress collagen destruction, and/or to increase collagen production are currently being developed. For discussions of investigations into such treatments, see for example the Curci article; "Are There Ways to Retard the Growth of Abdominal Aortic Aneurysms?" White, John V., 2001 Clinical Congress PG 10, Session IIA: New Approaches to Old Problems: Vascular Disease, 30-33 (hereinafter "White article"); "Indicators of infection with *Chlamydia pneumoniae* are associated with expansion of abdominal aortic aneurysms," Lindholt, Jes S., Ashton, Hillary A., et al., Journal of Vascular Surgery, August 2001, vol. 34, no. 2, 212-215 (hereinafter "Lindholt/ Ashton article"); "Randomized double-blind controlled trial of roxithromycin for prevention of abdominal aortic aneurysm expansion," Vammen, S., Lindholt, J. S., et al., British Journal of Surgery 2001, 88, 1066-1072 (hereinafter "Vammen article"); "Treatment of *Chlamydia pneumoniae* infection with roxithromycin and effect on neointima proliferation after coronary stent placement (ISAR-3): a randomized, double-blind, placebo-controlled trial," Neumann, Franz-Josef, Kasrati, Adnan, et al. The Lancet, Jun. 30, 2001, vol. 357, 2085-2089 (hereinafter "Neumann article"); "Five-year Results of Elastin and Collagen Markers as Predictive Tools in the Management of Small Abdominal Aortic Aneurysms," Lindholt, J. S., Heickendorff, L., et al., Eur J Vasc Endovasc Surg, March 2001, vol. 21, 235-240 (hereinafter "Lindholt/ Heikendorff article"); and "Antibodies Against *Chlamydia pneumoniae* Predict the Need for Elective Surgical Intervention on Small Abdominal Aortic Aneurysms," Vammen, S., Lindholt, J. S., et al., Eur J Vasc Endovasc Surg, August 2001, vol. 22, 165-168 (hereinafter "Vammen/Lindholt article"); the contents of all of the foregoing articles being hereby incorporated by reference.

As discussed in many of the above-referenced articles, scientists continue to research treatment of AAAs by administration of one or more systemic therapeutic agents. Some agents which have been tried include doxycycline, tetracycline, tetracycline derivatives, roxithromycin and propranolol. Such systemic treatments have shown significant levels of success, typically in vitro or in laboratory rats. Administration of agents on a systemic level, however, such as by oral or intravenous administration, has certain inherent drawbacks. The most obvious drawback to any medication is the unwanted side effects that accompany the drug. When a drug is given systemically to treat a localized medical condition, the dose of the drug is typically larger than would be ideal and, thus, has a greater likelihood of causing unwanted or harmful side effects. On the other hand, if a therapeutic drug used to treat a local condition is delivered locally at or near the treatment site, doses can usually be decreased to more tolerable levels.

In the pharmaceutical treatment of AAAs with antibiotics, antibiotic derivatives, propranolol and/or other agents, researchers have already found that beneficial effects appear to be dose dependent. (See, for example, the Curci article.) If sufficient doses of medications to treat AAAs are administered systemically, the medications are likely to have unwanted side effects. Listed side effects for doxycycline, for example, include anorexia, nausea, vomiting, diarrhea, rashes, kidney toxicity, and anemia. At the very least, antibiotic treatment may lead to unwanted antibiotic resistance, already a growing problem in the United States. Propranolol, which is commonly used to treat high blood pressure but has been found to have beneficial effects on AAAs, can cause slowed heart rate, lightheadedness, abnormally low blood pressure, depression, nausea, vomiting, abdominal cramping, bronchospasm, agranulocytosis, and/ or various other adverse effects in some people. Therefore, it would be advantageous to have methods and devices for delivering one or more therapeutic agents to a treatment area at or near a AAA. Such delivery may enhance medical therapy of AAAs while limiting adverse drug reactions in treated patients.

BRIEF SUMMARY OF THE INVENTION

Generally, the present invention provides methods and devices for treating aneurysms. Although many types of aneurysms may be treated with such methods and devices, such as cerebral, carotid and coronary aneurysms, the following discussion focuses on the treatment of abdominal aortic aneurysms ("AAAs"). More specifically, methods and devices provide for delivery of one or more therapeutic agents to a treatment area at or near a AAA in an effort to slow the dilation and weakening of a wall of the aorta.

In one aspect, a method for treating an aneurysm includes delivering at least one therapeutic agent at a location near the aneurysm. Optionally, such a method may include placing at least one device at a location near the aneurysm, where the therapeutic agent is releasably carried by the device and the device releases the therapeutic agent at a location near the aneurysm. For example, the device may include one or more prostheses, such as stents or grafts, for maintaining integrity of a portion of a blood vessel in which the aneurysm is located.

In some embodiments, typically where the device is configured to be placed within an abdominal aorta, the device may include a first stent member for anchoring the device in a location between the aneurysm and one or more renal arteries and a skirt member coupled near its proximal end with the first stent member and extending in a direction towards the aneurysm. Such embodiments may also include a second stent member coupled with the first stent member, where the second stent member further anchors the device in a location above the one or more renal arteries. In any of the above embodiments, one or more therapeutic agents may be carried by the first stent member, the second stent member, the skirt member, or any combination thereof.

In other embodiments, the device may include one or more balloons for delivering at least one therapeutic agent. For example, in some embodiments the device includes one balloon with one or more perforations configured to release the at least one therapeutic agent. In other embodiments, the therapeutic agent is coupled with an outer surface of the balloon. In still other embodiments, the device further includes a plurality of needles coupled with the balloon, the needles configured to facilitate delivery of the at least one therapeutic agent to a location within a blood vessel wall in which the aneurysm is located. And in yet other embodiments, the balloon may be a torroidally-shaped balloon for allowing blood flow to occur through a blood vessel in which the balloon is placed.

In some embodiments, the device may include an expandable wire basket. One or more sacs may be coupled with the wire basket such that the sacs release at least one therapeutic agent at a treatment site. In other embodiments, the device includes multiple capsules attachable to a blood vessel wall, the capsules being configured to release at least one therapeutic agent.

Any suitable therapeutic agent or combination of agents may be used in various methods of the present invention. For example, some agents which may be used include antibiotics or antibiotic derivatives such as doxycycline, tetracycline, roxithromycin and chemically modified tetracyclines, and collagen promoting agents such as propranolol. In some embodiments, two or more agents may be delivered. Optionally, one agent may be delivered before another, for example an antibiotic may be delivered before propranolol. Such sequential delivery may have advantageous treatment results.

The delivery of certain agents may also be combined. For example, the antibiotics described above may be first delivered in order to treat and inhibit bacterial infection, such as *C pneumoniae*, which can cause collagen destruction. Anti-inflammatory agents may also be introduced simultaneously or subsequent to the introduction of the antibiotics. After the infection and inflammation have been managed, it may be desirable to introduce collagen, gelatin, hydroxyapatite, or other known bulking agents in order to reinforce the aortic or other blood vessel wall.

In another aspect, a device for treating an aneurysm includes a drug delivery arrangement for delivering at least one therapeutic agent to a location near the aneurysm. In various embodiments, the drug delivery arrangement may include any suitable stent, graft, skirt, one or more iliac leg members, or any combination thereof, as described above. In other embodiments, also as described above, a drug delivery arrangement may include one or more inflatable balloons, a torroidal balloon, a balloon with perforations and/or needles, an expandable wire basket, multiple capsules or any suitable combination thereof. Incorporated into any one of these embodiments may be one or more therapeutic agents, such as doxycycline, tetracycline, roxithromycin, a chemically modified tetracycline, or propranolol.

In yet another aspect, a kit for treating an aneurysm may include a treatment device for placement in a blood vessel where the aneurysm is located, a placement device for use in placing the treatment device in the blood vessel, and instructions for using the treatment device and the placement device.

DETAILED DESCRIPTION OF THE INVENTION

Methods and devices of the present invention generally provide delivery of one or more therapeutic agents to a treatment site at or near an aneurysm, typically an abdominal aortic aneurysm ("AAA"). Many method embodiments include placing a device at or near an abdominal aorta and releasing one or more therapeutic agents from the device. However, the present invention contemplates methods for delivering one or more therapeutic agents to a treatment area at or near the abdominal aorta without first placing a device. For example, in one embodiment capsules may be distributed at a location within an abdominal aorta, the capsules being attachable to a blood vessel wall and carrying one or more therapeutic agents for distribution. Such capsules may be considered a "device" for the purposes of this application, but to the extent that they or other embodiments do not include a device, the present application should not be limited to methods including placement of a device.

Examples of therapeutic agents which may be used to treat AAAs include antibiotics and antibiotic derivatives such as doxycycline, roxithromycin, tetracycline and tetracycline derivatives, and collagen promoting agents such as propranolol. Other agents now known to enhance aneurysm therapy or discovered in the future may be similarly used with the present invention. Some embodiments include releasing multiple agents simultaneously or in sequential fashion. Devices for agent delivery may include prostheses such as stents and grafts, balloons with perforations and/or needles, expandable wire baskets, drug-eluting capsules, suitable combinations thereof, or any other suitable device or combination. One embodiment, for example, includes a stent with a distally-extending skirt and an supra-renal anchor.

Figure 1:
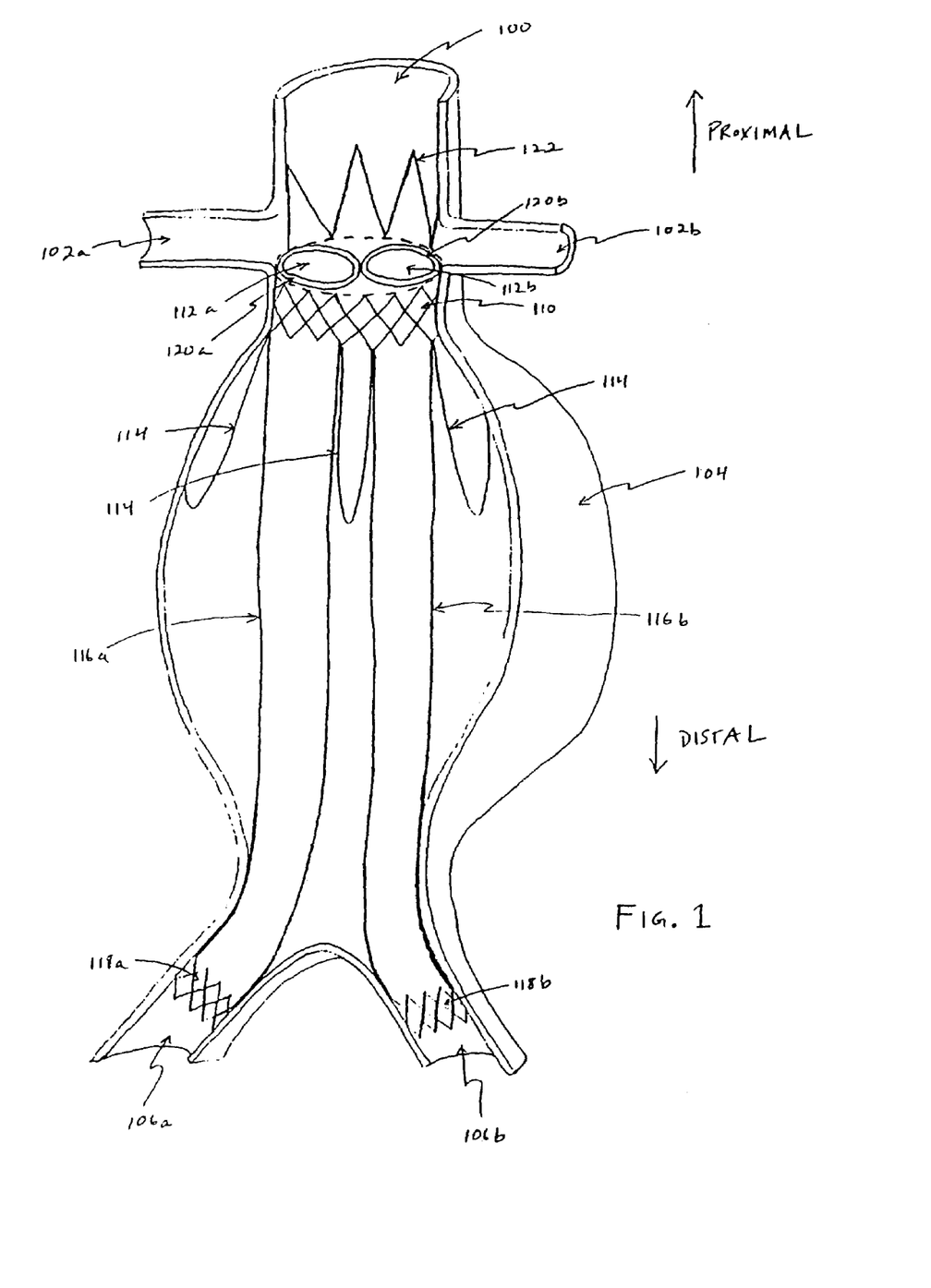
FIG. 1 is a cross-sectional perspective view of a device for local delivery of therapeutic agents, in a treatment location within a AAA, according to one embodiment of the present invention.

Referring now to FIG. 1, an aorta 100 is shown with a right renal artery 102a, a left renal artery 102b, an aneurysm 104 in the wall of the aorta, a right iliac artery 106a and a left iliac artery 106b. One embodiment of a device for treating aneurysm 104 suitably includes a first stent member 110, with a right tubular member 120a forming a right lumen 112a and a left tubular member 120b forming a left lumen 112b. Although illustrated as separate tubular members 120a and 120b, the separate tubes could be joined into a common tubular body at least at their upper ends prior to separating into isolated branches which enter each of the iliac arteries below. This embodiment also includes a skirt 114 extending distally from first stent member 110, a second stent member 122 extending proximally from first stent member 110 and two iliac leg members 116a, 116b attached to and extending distally from first stent member 110. Each iliac leg 116a, 116b, in turn, includes an iliac anchoring stent 118a, 118b.

It should be emphasized that FIG. 1 describes only one exemplary embodiment and that many different embodiments for a drug delivery device to the abdominal aorta are contemplated within the scope of the invention. For example, some embodiments may include only stents, some embodiments do not include second stent member 122, some embodiments do not include iliac legs 116a, 116b and those legs may be provided and attached separately, other embodiments use differently configured skirts, and/or the like. The legs 116a and 116b may also be fully supported by stent or other scaffold structures along their entire length or over additional portions of their lengths between the terminal stents 110, 118a, and 118b. Also, as previously discussed above, this and other embodiments may be used or adapted for use in blood vessels other than the abdominal aorta, such as the carotid arteries, coronary arteries, cerebral vessels, and/or the like.

That being said, first stent 110 is generally configured to anchor the device by attaching to the wall of aorta 100 at a location between aneurysm 104 and renal arteries 102a, 102b. First stent 110 may thus include any device or combination of devices suitable for anchoring the overall device to a vessel wall. For example, in various embodiments first stent 110 may be entirely self-expanding, entirely balloon expandable or a combination of self-expanding and balloon expandable. In one embodiment, for example, alternating sections of first stent 110 are made of nitinol, a self-expanding material, and stainless steel, a balloon expandable material. In FIG. 1, for example, alternating diamond-shaped sections of first stent 110 could be made from different materials. Such a combination may provide for a conveniently self-expanding stent which could be further expanded by a balloon, to attach securely to the wall of the aorta and prevent leakage of blood around the device. Many other materials and configurations for making a stent are commonly know to those skilled in the art and any suitable combination of materials, configurations, sizes and the like may be used to make first stent member 110. Alternatively, separate expansible stent sections or scaffolds may be laminated to each other such that the overall stent will have a combination of deformable and elastic characteristics. The different layers may be laminated along their entire interface surface, or otherwise held together at different discrete points about their common circumferential interface.

Tubular member 120 is attached to stent 110 and is then joined at the center to form separate legs 120a and 120b to form two lumens 112a, 112b. Such lumens 112a, 112b typically provide for attachment to first stent member 110 of two iliac legs 116a, 116b, so that tubular members 120a, 120b may direct blood flow into the legs 116a, 116b. Materials used to make grafts, such as polytetrafluoroethylene (PTFE) and other polymers, are well known to those skilled in the art and any suitable material may be used for tubular member 120. In some embodiments other grafts may be attached to first stent member 110, such as a graft on the outside of the stent and the like.

Skirt 114 extends distally from first stent member 110 and typically is configured to be positioned in contact with the inner wall of aorta 100. In various embodiments, skirt 114 may be made of all stent material, all graft material, or a combination of stent and graft material. As pictured in FIG. 1, skirt 114 is a relatively freely-hanging graft material which may be placed in contact with the inner wall of aorta 100. In other embodiments, skirt 114 includes multiple stent-like legs and no graft material. Any suitable configuration is contemplated.

Second stent member 122 is generally any stent configuration capable of further anchoring the device by attaching to a location proximal to renal arteries 102a, 102b—i.e., in a suprarenal location. Typically, second stent member 122 will include only stent material, so that blood flow through the device to renal arteries 102a, 102b is not reduced. However, second stent members 122 including graft material or other suitable materials are contemplated. As with first stent member 110, any suitable material, such as nitinol, stainless steel, a combination thereof, or the like, may be used to make second stent member 122. The second stent member 122 may be formed integrally with the first stent member 110 or may be formed as a discrete scaffold component which is either attached or unattached to stent 110.

Iliac legs 116a, 116b may be a part of the device or may be provided separately from the device. Typically, iliac legs 116a, 116b will be positioned at the treatment area and attached to first stent member 110 after stent member 110 is in place. In some embodiments, however, iliac legs 116a, 116b may be pre-attached to first stent member 110 before insertion, may be attached to another component of the device, such as skirt 114, or the like. Generally, iliac legs 116a, 116b are anchored to iliac arteries 106a, 106b by iliac anchors 118a, 118b. Both legs 116a, 116b and anchors 118a, 118b may include any suitable combination of stent materials and/or graft materials, as previously discussed above in relation to first stent member 110. The legs 116a and 116b, as discussed above, are shown to be supported by stents only at their ends. Alternatively, the legs may be fully supported or additionally supported over the entire length or a portion thereof. Other supports are possible, including axial elements, discrete ring members attached to the legs, and the like.

Any component or combination of components of the device as described above and in FIG. 1 may be used to deliver one or more therapeutic agents to an area at or near abdominal aorta 100 to treat aneurysm 104. In some embodiments, for example, only first stent member 110 may carry a therapeutic agent. In other embodiments, first stent member 110 and skirt 114 may carry an agent. In still other embodiments, every element of the device shown in FIG. 1 may carry a therapeutic agent or agents.

Additionally, one or more components may deliver one or more therapeutic agents by any of a number of suitable means. In some embodiments, for example, a drug may be delivered by coating a component with the drug, wherein the drug is released when the component is exposed to the vascular environment of the treatment area. In other embodiments, a device component may include micropores and/or discrete reservoirs for carrying and releasing one or more drugs. Such micropores or reservoirs may be designed to release multiple drugs in a sequence, for example to release an antibiotic followed by a collagen promoting agent. When reservoirs are employed, release rate controlling membranes or other structures can be positioned over an opening of the reservoir to provide for a desired release rate over time. In still other embodiments, a surface of a component may include small spikes to enhance delivery of a drug into a blood vessel wall. Thus, any suitable device configuration for delivering one or more therapeutic agents to an area within or near an abdominal aorta is contemplated by the present invention.

As described thus far, the aneurysmal drug delivery devices have been implantable. The methods of the present invention, however, may also be performed with non-implantable structures, such as catheters, which are temporarily introduced to the aneurysmal target site for treatment. Usually, the catheters will be intravascularly introduced, typically through a cut down or through the well-known Seldinger technique. The catheters will comprise a catheter body, typically which is introducable over a steerable guidewire. At a distal end of the catheter, a structure will be provided to perform the desired drug delivery.

Figure 2:
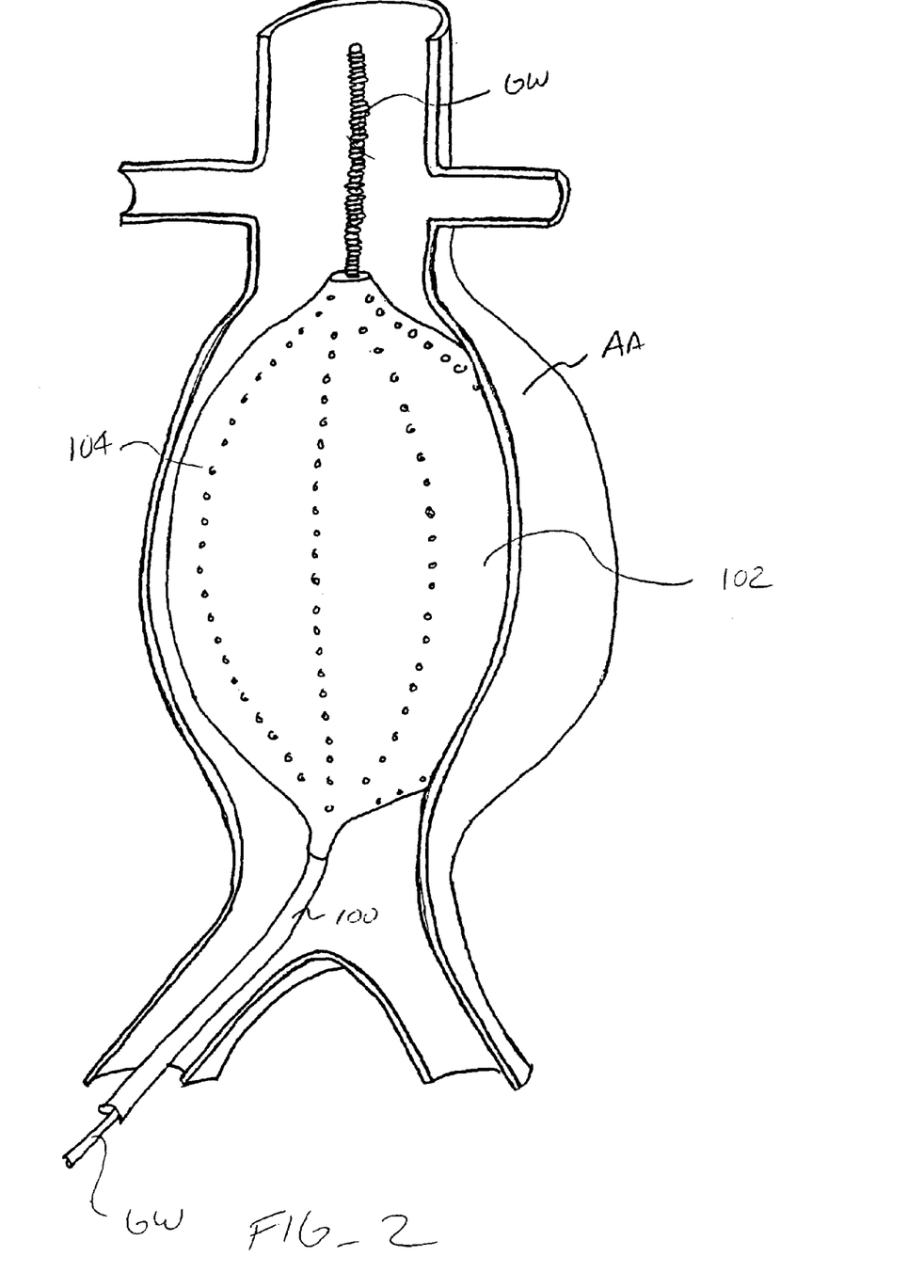
FIGS. 2-7 illustrate a variety of catheter-based aneurysmal drug delivery systems suitable for performing the methods of the present invention.

Referring now to FIG. 2, the drugs may be delivered by a catheter 100 having a perforated balloon 102 at its distal end. The catheter may be introduced over a guidewire to the target site, which is illustrated as an aortic aneurysm AA. The drugs may be introduced to inflate the balloon and, once a sufficient pressure is relieved, to pass outwardly through the perforations 104 formed in a pre-selected pattern over the balloon surface. Usually, the perforations will be evenly distributed over the surface of the balloon, but there may be instances when asymmetric delivery is desired for some reason. While the drug or drug-carrying solution will usually be the balloon inflation medium, it will also be possible to separately inflate the balloon and to deliver drugs through isolated lumen(s) formed in the balloon structure and/or catheter body.

Figure 3:
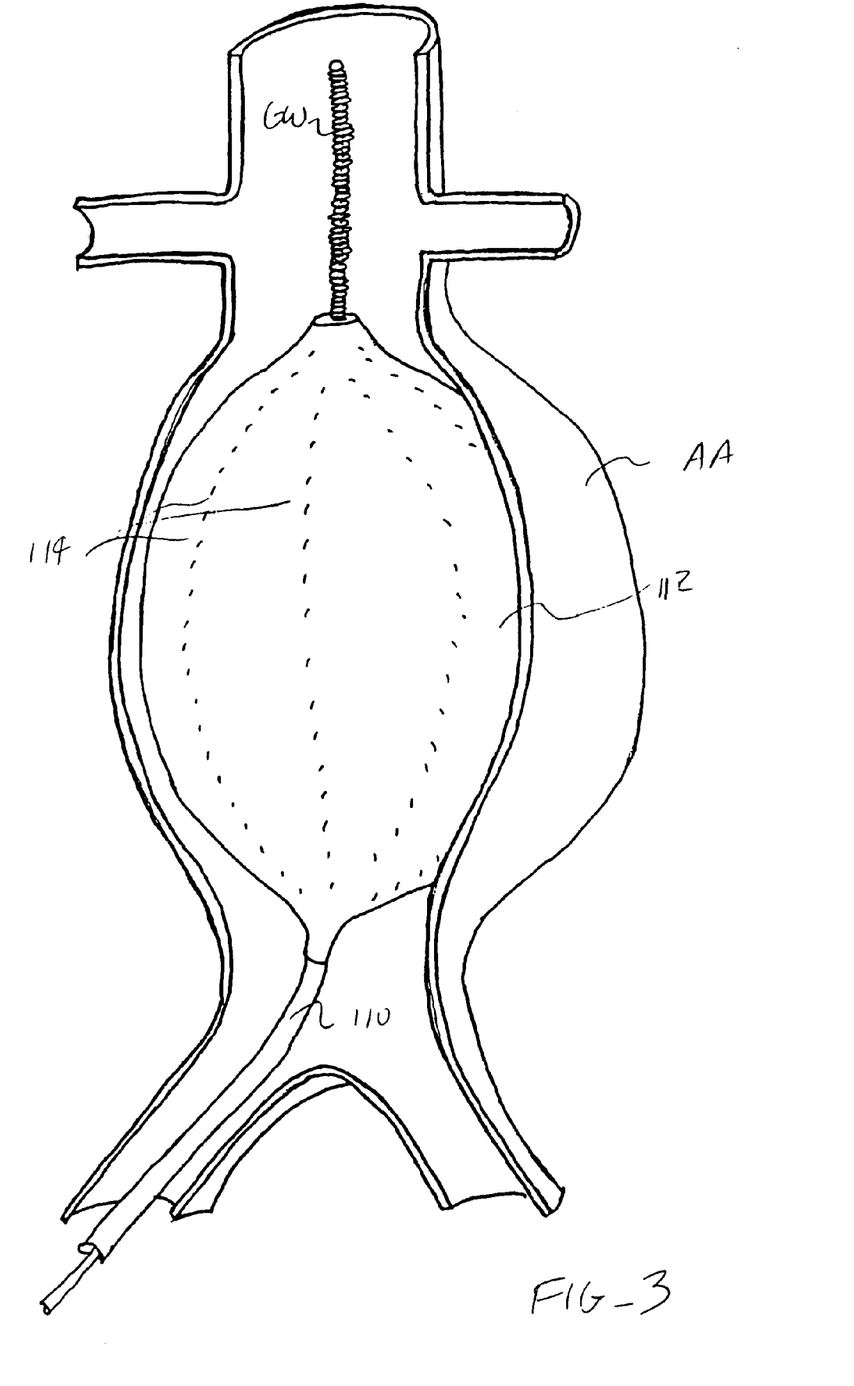

Referring now to FIG. 3, a catheter 110 which is also introducable over a guidewire GW is positioned to treat an aortic aneurysm AA. The catheter has an inflatable balloon 112 at its distal end, and the balloon has a plurality of microneedles 114 formed over its surface. The catheter may be operated to deliver the drug medium in manner analogous to that described with respect to FIG. 2, i.e., the medium may be used to inflate the balloon and, once a threshold pressure has been reached, be delivered through the microneedles which have penetrated into the aneurysmal wall. Alternatively, separate delivery means may be provided within the catheter in the balloon for delivering the medium through the needles 114 at a different pressure.

Figure 4A:
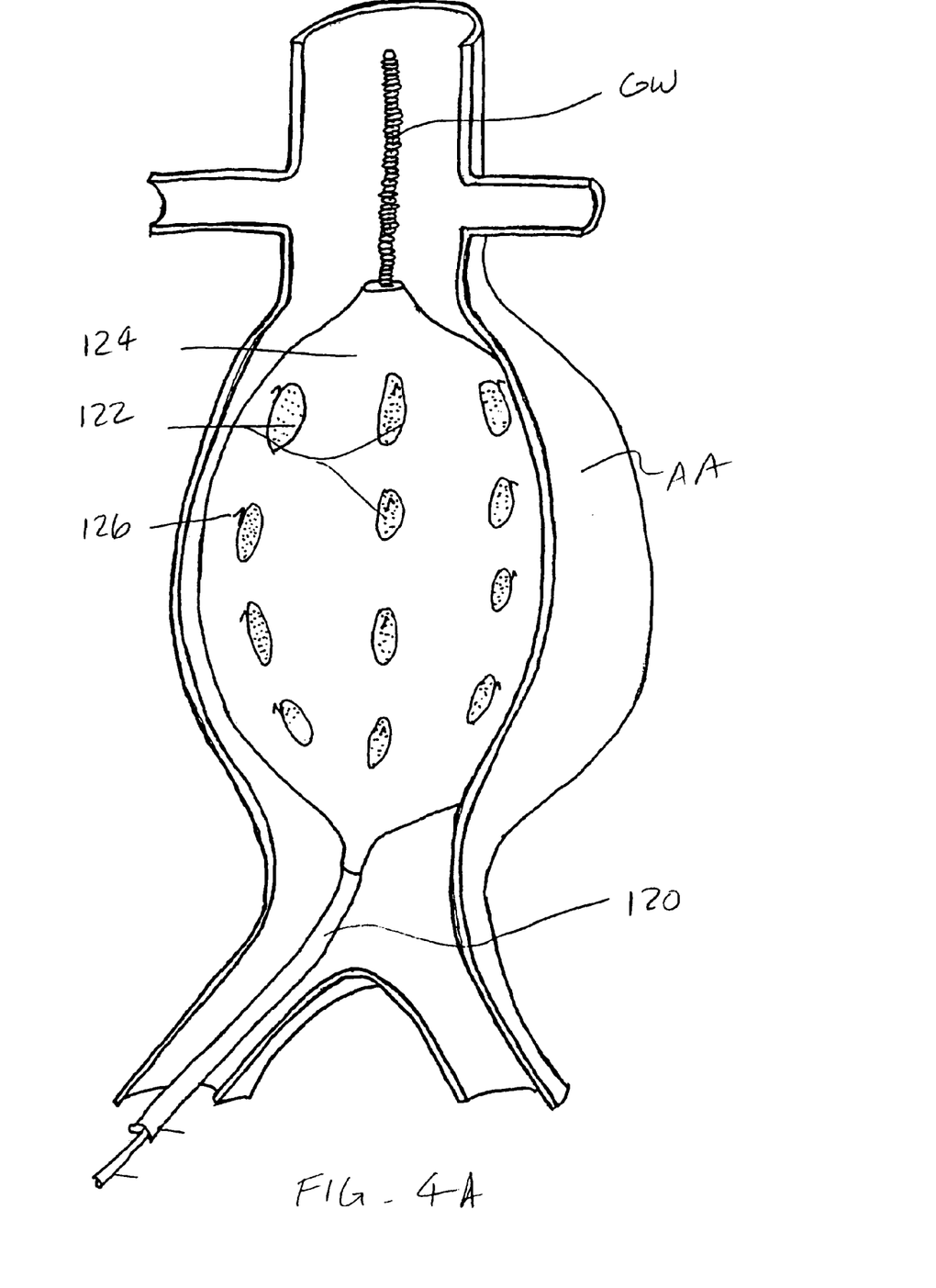
Figure 4B:
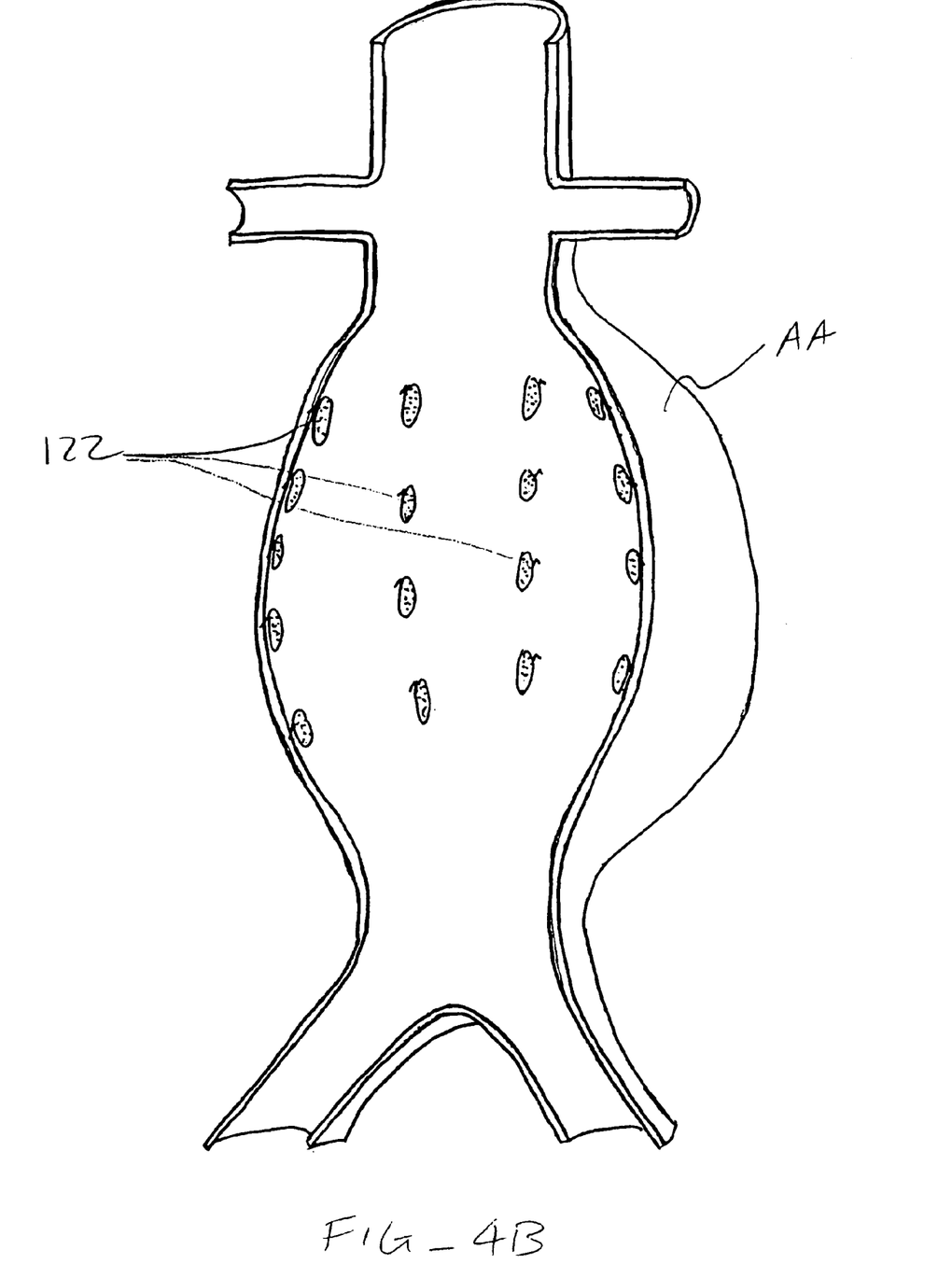

Referring now to FIG. 4, a catheter 120 may be utilized to deliver a plurality of drug delivery capsules 122 which are initially disposed over an exterior surface of an inflatable balloon 124, as illustrated in FIG. 4a. The catheter 120 may be positioned over a guidewire GW at the aortic aneurysm AA, as described previously. By inflating the balloon 124, the drug capsules 122 are implanted into the interior wall of the aneurysm AA, as illustrated in FIG. 4b. Catheter 120 may then be removed, leaving the drug capsules 122 in place. The drug capsules may be any of a variety of conventional controlled drug delivery structures intended to release the desired drug into the aneurysmal wall over time at a controlled rate. Optionally, the capsules may comprise hooks 126 (FIG. 4a) or other similar anchors for holding the capsules in the wall.

Figure 5:
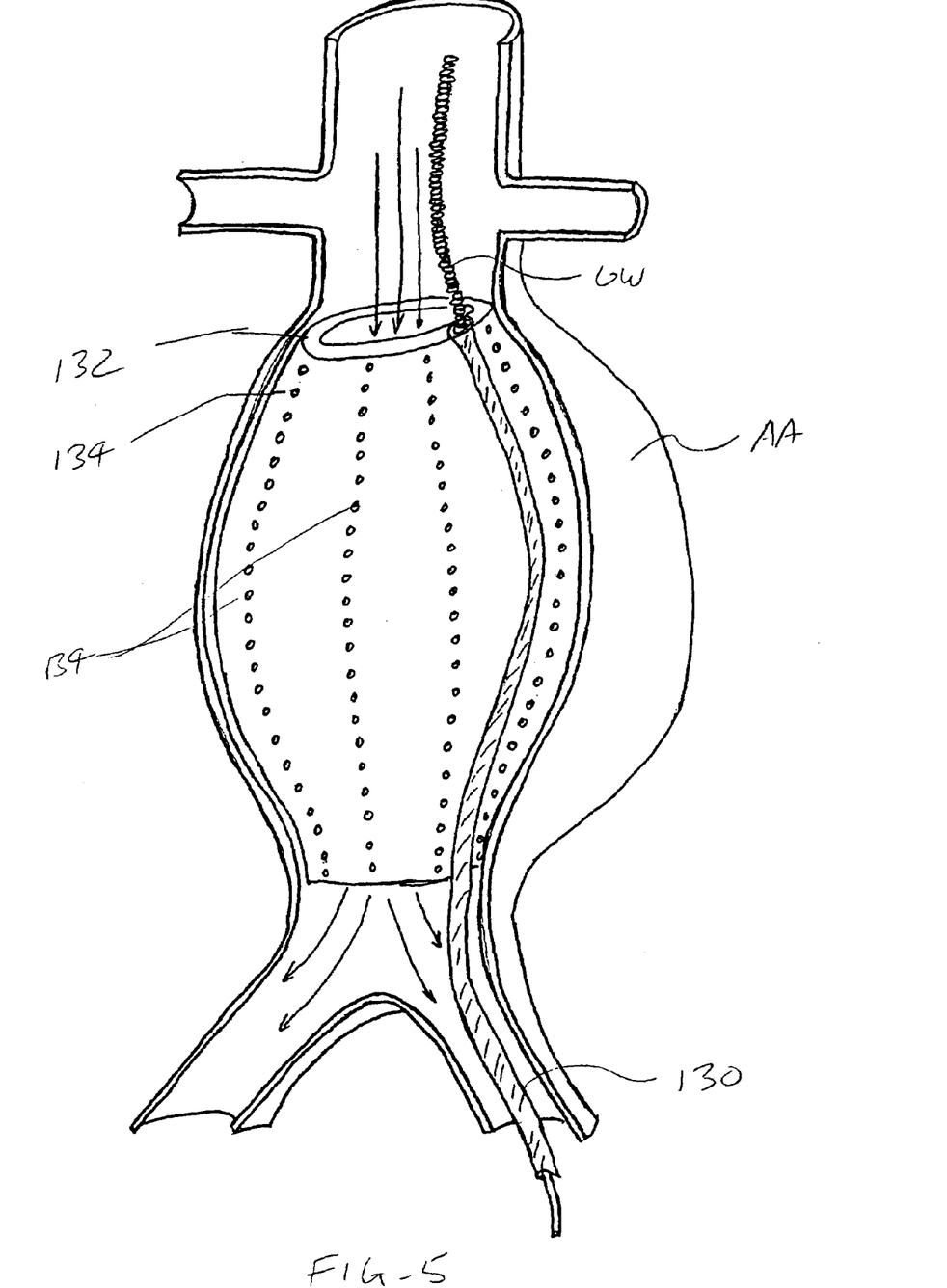

Referring now to FIG. 5, a catheter 130 includes a torroidal balloon 132 at its distal end. The catheter may be introduced over a guidewire GW to the aortic aneurysm AA generally as described previously. The drug may be delivered through perforations 134 formed in the torroidal balloon 132, where the drug may be used to inflate the balloon or alternatively may be delivered through separate, isolated delivery lumens in the balloon and the catheter. An advantage of the torroidal balloon structure is that it allows blood flow through its center during balloon deployment and drug delivery.

Figure 6:
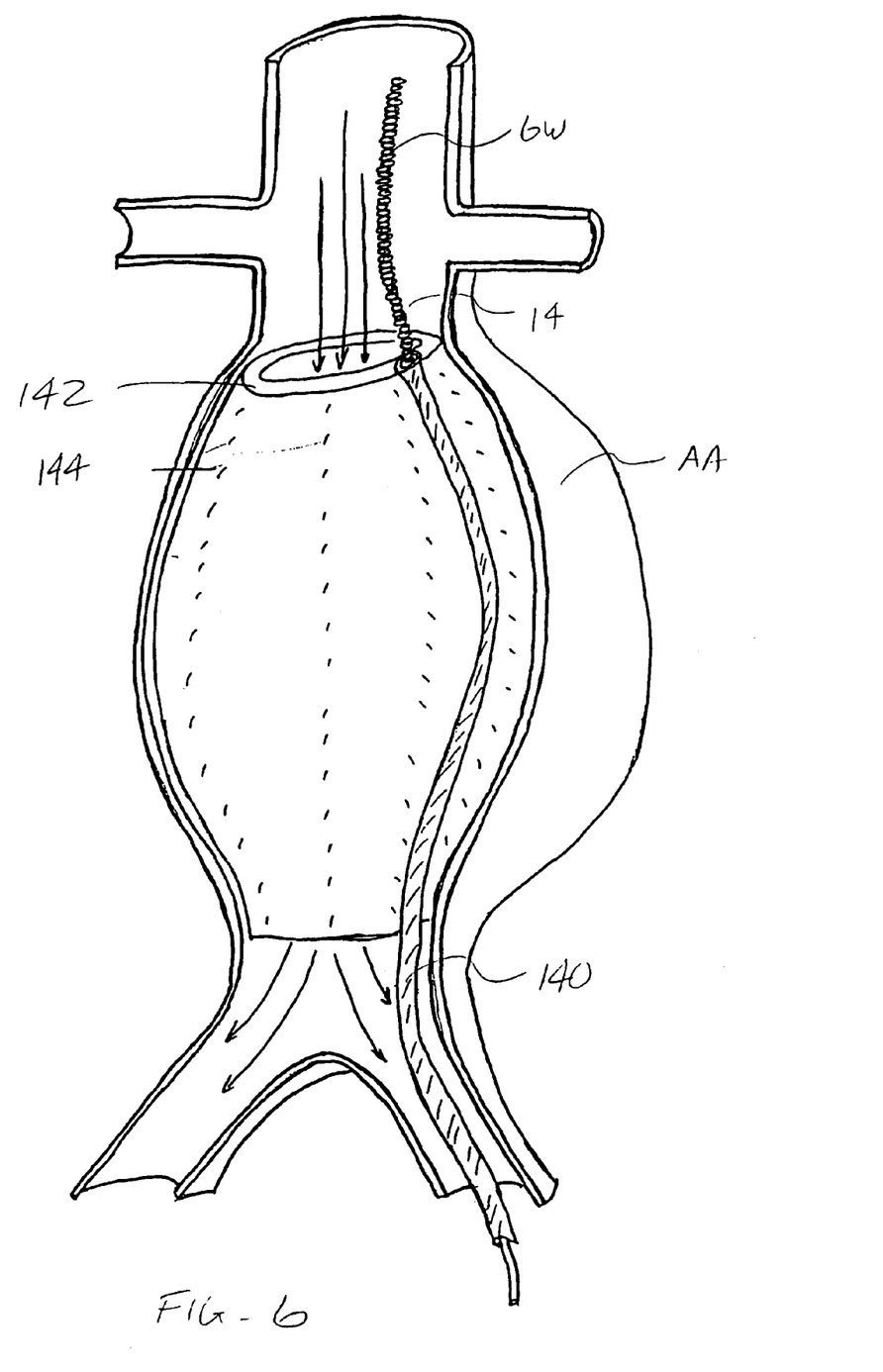

Referring now to FIG. 6, a catheter 140 includes a torroidal balloon 142 similar to that described in connection with catheter 130 above. Instead of perfusion holes, however, catheter 140 has microneedles 144 formed over its exterior surface. Catheter 140 is also intended for introducing to an aortic aneurysm AA over a guidewire GW, as previously discussed, and permits blood perfusion through the axial opening in the balloon 142. As with previous embodiments, the drug to be delivered may also serve as the inflation medium for the balloon 142. Alternatively, the drug may be delivered to the microneedles 144 via isolated lumens formed within the balloon and/or catheter.

Figure 7:
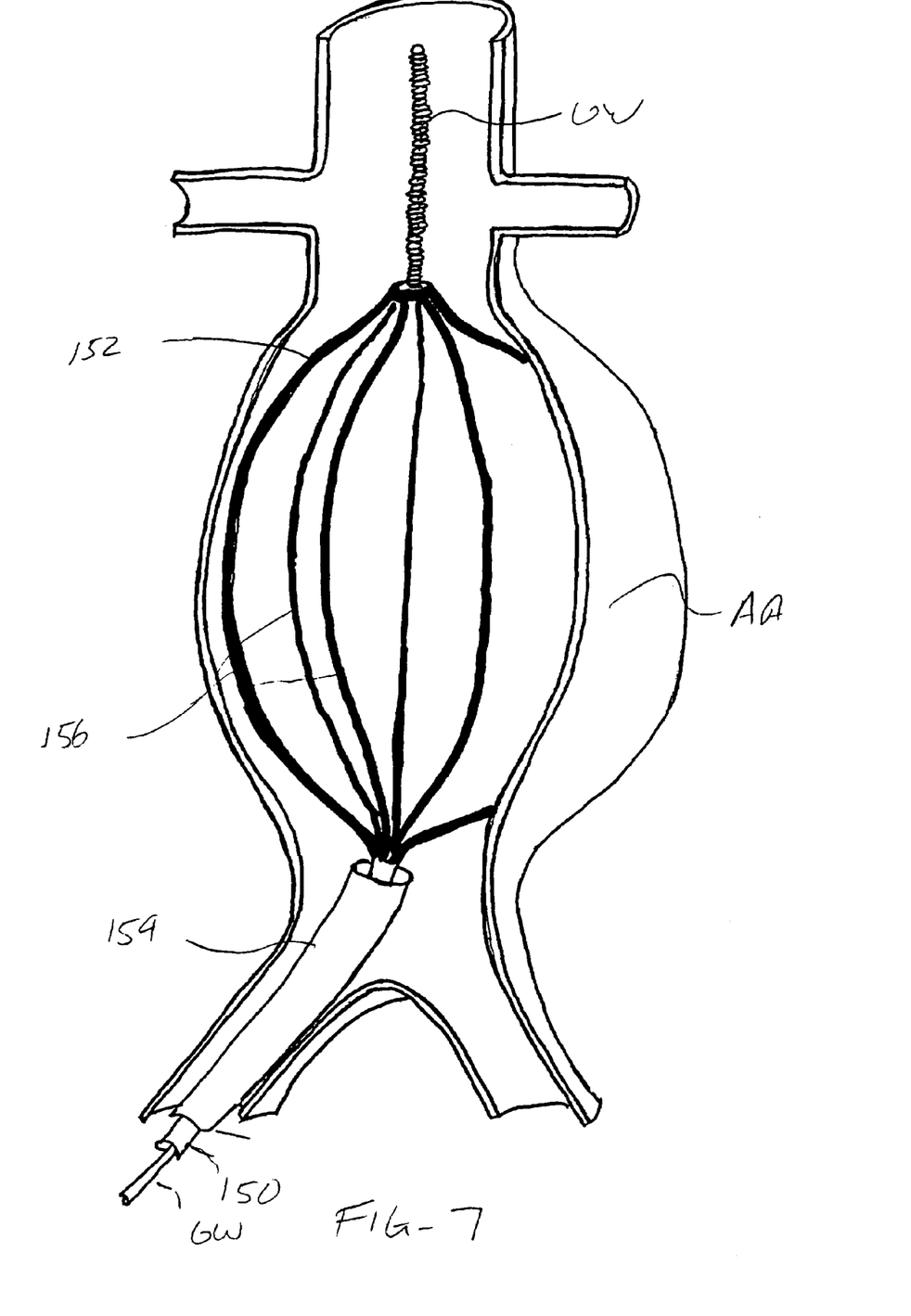

Referring now to FIG. 7, drugs may be delivered according to the methods of the present invention using a catheter 150 introducable over a guidewire GW. The catheter 150 carries an expansible cage 152 at its distal end. As illustrated, the cage is constructed from elastic struts or tubes, typically formed from a shape memory alloy, such as a nickel-titanium alloy. Typically, the elastic struts will be coated with drugs, and the cage may be released and implanted in the manner of a stent. Alternatively, the tubes include lumens for infusing the drug to be delivered. The cage may be selectively expanded and collapsed by withdrawing or extending the cage from a cover sheath 154. The drugs may be delivered through the longitudinal elements 156 of the sheath through holes, microneedles, or other release (not shown).

Although FIG. 1 and the foregoing discussion describe a device for AAA treatment which may generally be described as a stent assembly, many other suitable devices are contemplated for treating AAAs by delivering therapeutic agents to the abdominal aorta. For example, some embodiments include an inflatable balloon device. Such a device may be coated with one or more agents, may have perforations to distribute agents, may have micro-spikes on its surface for enhancing distribution of agents into a vessel wall, and/or the like. In some embodiments, a balloon with a torroidal shape may be used, to allow flow of blood through the center of the balloon while the balloon is in a location for treatment.

Other embodiments may include an expandable wire basket, with the basket being coated with a drug, having micropores for drug distribution, or the like. Alternatively, a basket may include attachable small sacs for containing and distributing one or more agents. In one embodiment, the basket includes longitudinal leg-like members that join at a common base member. In such embodiments, the basket is delivered by removing a deployment sheath from around the basket and allowing it to expand in the treatment area. Such a basket may be removable after drug delivery is completed to may be detachable for permanent implantation and chronic drug delivery, optionally being capable of being reloaded in situ using appropriate catheters or other devices.

In still other embodiments, small capsules or similar devices may be distributed within an abdominal aorta. Such capsules may be configured to attach to the wall of the aorta to distribute one or more agents. In one embodiment, for example, such capsules may include small hooks for attaching to the aortic wall. The capsules may be delivered to a treatment area by any suitable means, such as by an expandable delivery balloon. In other embodiments, one or more therapeutic agents may be injected into the treatment area directly. Such agents may be used alone or may be coupled with an attachment substance to allow the agents to adhere to the wall of the aorta.

As described above, any suitable therapeutic agent or combination of therapeutic agents may be used with devices and methods of the present invention. For example, an anti-elastolytic enzyme drug may be used, a collagen promoting agent may be used, or a combination of both may be used. Examples of drugs which act against elastolytic enzymes and similar enzymes include, but are not limited to, doxycycline, roxithromycin, tetracycline, and tetracycline derivatives. One collagen promoting agent which is presently being researched for treatment of AAAs is propranolol, but any other collagen promoting agent may be used. In fact, any other agents now known to enhance aneurysm therapy or discovered in the future may be similarly used with the present invention.

As discussed briefly above, in some embodiments it may be advantageous to deliver two or more therapeutic agents in sequential fashion. This may be accomplished by any suitable device or method. In one embodiment, for example, a device may contain two or more agents in micropores or reservoirs. The agents may have different molecular sizes such that they will be released from the micropores or reservoirs at different rates. In other embodiments, multiple agents may be placed into a containment device such as micropores or reservoirs in an order, such that the agents are then also released in a desired order. Alternatively, reservoirs may include a rate-controlling membranes, as described above.

Although exemplary embodiments of methods and devices have been disclosed herein, it should be apparent from the foregoing description that variations and modifications of such embodiments may be made without departing from the scope of the invention. Therefore, the above description should not be taken as limiting the scope of the invention which is defined by the appended claims.

What is claimed is:

1. A method for treating an aneurysm within an aorta, the method comprising implanting a device comprising a stent member and a therapeutic agent-carrying member such that the stent is anchored adjacent one or more renal arteries and the therapeutic agent-carrying member extends toward the aneurysm, wherein the member comprises a skirt extending from the stent member into the aneurysm and contacting an inner wall of the aorta to release at least one therapeutic agent outwardly to a location on an aortic wall in the aneurysm, wherein the therapeutic agent slows dilation and weakening of the wall of the aorta.

2. The method of claim 1, wherein, the aneurysm is an abdominal aortic aneurysm.

3. The method of claim 1, wherein the at least one therapeutic is taken from the group consisting of doxycycline, tetracycline, roxithromycin, a chemically modified tetracycline, and propranolol.

4. The method of claim 1, further comprising delivering at least a second therapeutic agent.

5. The method of claim 4, wherein the first agent is delivered before the second agent.

6. The method of claim 4, wherein the first therapeutic agent is an antibiotic and the second therapeutic agent is a collagen promoting agent.

7. A device for delivering at least one therapeutic agent to a location near the aneurysm, said device comprising:
an anchor;
a pair of iliac legs extending from the anchor; and
a therapeutic agent-carrying member extending from the anchor and disposed about the iliac legs, wherein the therapeutic agent-carrying member carries the therapeutic agent and the anchor and are configured so that the therapeutic agent-carrying member comprises a skin extending from the anchor into the aneurysm to contact a wall of the aneurysm when the anchor is implanted adjacent to the aneurysm and the iliac legs extend into the aneurysm.

8. The device of claim 7, wherein the anchor comprises at least one stent member for maintaining patency of at least a portion of a blood vessel in which the aneurysm is located.

9. The device of claim 8, wherein at least one stent member and the therapeutic agent-carrying member is configured to be attachable to at least one leg member, the leg member configured to connect the device to at least one iliac artery.

10. The device of claim 7, wherein the drug delivery arrangement is configured to be placed within an abdominal aorta.

11. The device of claim 10, further comprising a second anchor for further anchoring the device in a location above the one or more renal arteries.

12. The device of claim 11, wherein at least one of the anchors includes a self-expanding portion and balloon expandable portion.

13. The device of claim 10, wherein the at least one therapeutic agent is also carried by the anchor.

14. The device of claim 7, wherein the therapeutic agent-carrying member is configured to contact a wall of an abdominal aortic aneurysm.

15. The device of claim 7, wherein the at least one therapeutic agent is selected from the group consisting of doxycycline, tetracycline, roxithromycin, a chemically modified tetracycline, and propranolol.

16. The device of claim 7, wherein the at least one therapeutic agent comprises an antibiotic and a collagen promoting agent and the device is configured to deliver the antibiotic to the location near the aneurysm before the collagen promoting agent is delivered.

* * * * *